(12) United States Patent  (10) Patent No.: US 7,748,900 B2
Maschke  (45) Date of Patent: Jul. 6, 2010

(54) X-RAY SYSTEM WITH AN INDUSTRIAL ROBOT

(75) Inventor: Michael Maschke, Lonnerstadt (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/827,015

(22) Filed: Jul. 10, 2007

(65) Prior Publication Data
US 2008/0013692 A1 Jan. 17, 2008

(30) Foreign Application Priority Data
Jul. 11, 2006 (DE) .................... 10 2006 032 094

(51) Int. Cl.
*H05G 1/02* (2006.01)

(52) U.S. Cl. .................. 378/198; 378/189; 378/193; 378/196; 378/197

(58) Field of Classification Search .............. 378/189, 378/198
See application file for complete search history.

(56) References Cited

U.S. PATENT DOCUMENTS

| | | | |
|---|---|---|---|
| 4,894,855 A | 1/1990 | Kresse | |
| 5,521,957 A * | 5/1996 | Hansen | 378/198 |
| 5,627,873 A * | 5/1997 | Hanover et al. | 378/197 |
| 5,835,558 A | 11/1998 | Maschke | |
| 6,609,826 B1 * | 8/2003 | Fujii et al. | 378/198 |
| 6,814,489 B2 * | 11/2004 | Jensen et al. | 378/197 |
| 2001/0005410 A1 * | 6/2001 | Rasche et al. | 378/197 |
| 2001/0022834 A1 * | 9/2001 | Graumann et al. | 378/198 |
| 2002/0150215 A1 * | 10/2002 | Barnes et al. | 378/197 |
| 2003/0039333 A1 * | 2/2003 | Houska et al. | 378/97 |
| 2004/0119597 A1 * | 6/2004 | Petzold et al. | 340/679 |
| 2004/0170255 A1 * | 9/2004 | Akutsu et al. | 378/197 |
| 2004/0234039 A1 * | 11/2004 | Karaus et al. | 378/196 |
| 2004/0258210 A1 | 12/2004 | Ritter | |
| 2006/0120511 A1 * | 6/2006 | Gregerson et al. | 378/198 |
| 2007/0003014 A1 | 1/2007 | Boese et al. | |

FOREIGN PATENT DOCUMENTS

| | | | |
|---|---|---|---|
| DE | 19708984 A1 * | 10/1998 | |
| DE | 19627657 C2 | 1/2003 | |
| DE | 10317137 A1 | 11/2004 | |
| DE | 10 2005 012 700 A1 | 9/2006 | |
| DE | 102005030609 A1 | 1/2007 | |
| EP | 0 220 501 B1 | 5/1987 | |

* cited by examiner

*Primary Examiner*—Hoon Song
*Assistant Examiner*—Mona M Sanei

(57) ABSTRACT

There is described an x-ray system with an x-ray source, an x-ray detector and at least one industrial robot having at least three, in particular six, axes of rotation, in which the x-ray source and/or the x-ray detector are/is arranged, directly or by means of a bearer, on the industrial robot, and where the industrial robot is constructed to be mobile, in particular is arranged on a device trolley.

16 Claims, 4 Drawing Sheets

X-RAY SYSTEM WITH AN INDUSTRIAL ROBOT

CROSS REFERENCE TO RELATED APPLICATIONS

This application claims priority of German application No. 10 2006 032 094.8 filed Jul. 11, 2006, which is incorporated by reference herein in its entirety.

FIELD OF INVENTION

The invention relates to an x-ray system with an x-ray source, an x-ray detector and at least one industrial robot having at least three, in particular six, axes of rotation, as claimed in claim 1.

BACKGROUND OF INVENTION

In x-ray imaging, x-ray systems are known in which, for the purpose of improved mobility, a trolley is provided with a C-arm affixed so that it can move, where an x-ray source and an x-ray detector are mounted on the C-arm, arranged opposite to one another. When this x-ray facility is used, for example in an operating theatre, the trolley is pushed up to an operating table on which the patient is held. After the x-ray images have been produced, the trolley is pushed away again to improve the access to the patient. An x-ray system of this type is, for example, known from US 20040258210 A1.

In order to ensure the freest possible access to the patient, the mounting of an x-ray tube on a first robot arm, which is affixed to a ceiling in an examination area, is known from EP 0 220 501 B1. An x-ray detector is mounted on a second robot arm which is affixed to a floor of the examination area, underneath the examination table. Each of the robot arms has two lever arms and three joints, and can be adjusted at the three joints. For the purpose of mutual adjustment of the x-ray source and the x-ray detector, a special controller is provided for moving the robot arms in coordination.

SUMMARY OF INVENTION

An object of the present invention is to devise an x-ray system which offers especially good access to the patient and at the same time is flexible in its application capabilities.

This object is achieved in accordance with the invention by an x-ray system with an x-ray source, an x-ray detector and at least one industrial robot having at least three, in particular six, axes of rotation, in accordance with an independent claim; advantageous embodiments of the invention are the subject of further claims.

In accordance with the invention, an x-ray system is produced by the mobile arrangement of the at least one industrial robot, having at least three and preferably six axes of rotation, on which are arranged an x-ray source and/or an x-ray detector, which can also be deployed temporarily at different places and in arbitrary positions. Hence, the x-ray system in accordance with the invention can easily be moved to patients who are not fit to be transported, and in particular the industrial robot with its six axes of rotation has six degrees of freedom, and thus a particularly high maneuverability, so that even the most complicated recording positions can be adopted. In turn this means less unpleasant repositioning for the patient, and opens up the possibility of applications which hitherto could not be carried out.

The term industrial robot is standardized in the EN775 norm. An industrial robot with six axes of rotation is referred to as a 6-axis vertical buckling arm robot.

The German patent application 10 2005 012 700.2, which is incorporated by reference herein in its entirety, shows an x-ray facility in which an x-ray source and an x-ray detector are mounted on a common bearer, which can be rotated about an axis of rotation, and are arranged opposite each other and aligned along the axis of rotation, and the bearer is mounted on the hand of an industrial robot which has six axes of rotation.

It is advantageous if the x-ray system has two independent industrial robots having at least three, in particular six, axes of rotation, with the x-ray source and the x-ray detector each being arranged on an industrial robot. This makes it possible to use the x-ray source and x-ray detector independently, thus extending the range of possible uses of the x-ray system. For example, the x-ray source can also be used with a second x-ray detector, for example a portable one. In such a case a system controller is responsible for sequences of movements which are aligned with each other.

According to one embodiment of the invention, the at least one industrial robot is arranged on a device trolley. Device trolleys offer a particularly flexible form of mobility, because they are not linked to guidance facilities, and can be used at no cost in different rooms or buildings. It is advantageous if the device trolley can be driven automatically or manually, in particular by means of a motor.

According to a further embodiment of the invention, the x-ray source and the x-ray detector are arranged jointly, using a bearer, on a hand of the industrial robot. This ensures that the x-ray source and the x-ray detector are permanently in exact alignment with each other, so that expensive readjustments are unnecessary and a rapid x-ray examination of high quality is guaranteed. In accordance with particularly advantageous embodiments of the invention, the bearer takes the form of a C-arm or a U-bracket, and the x-ray source is arranged at one end of the bearer and the x-ray detector at the relevant opposite end of the bearer.

It is advantageous if the x-ray system has a collision monitoring system and at least one collision sensor for monitoring the movements of the industrial robot. This increases the safety of the x-ray system in respect of the risk of injury to the operating staff and the danger of damage to device components.

It is advantageous if the x-ray system has a stability monitoring system and at least one stability sensor, by which the stability of the device trolley can be checked. This prevents damage which can arise from the collapse or tipping over of the x-ray system or the industrial robot.

BRIEF DESCRIPTION OF THE DRAWINGS

The invention, together with further advantageous embodiments in accordance with the characteristics of the subclaims, are explained in more detail below by reference to exemplary embodiments shown in schematic form in the drawing, without thereby limiting the invention to these exemplary embodiments, in which;

DETAILED DESCRIPTION OF INVENTION

Figure 1:
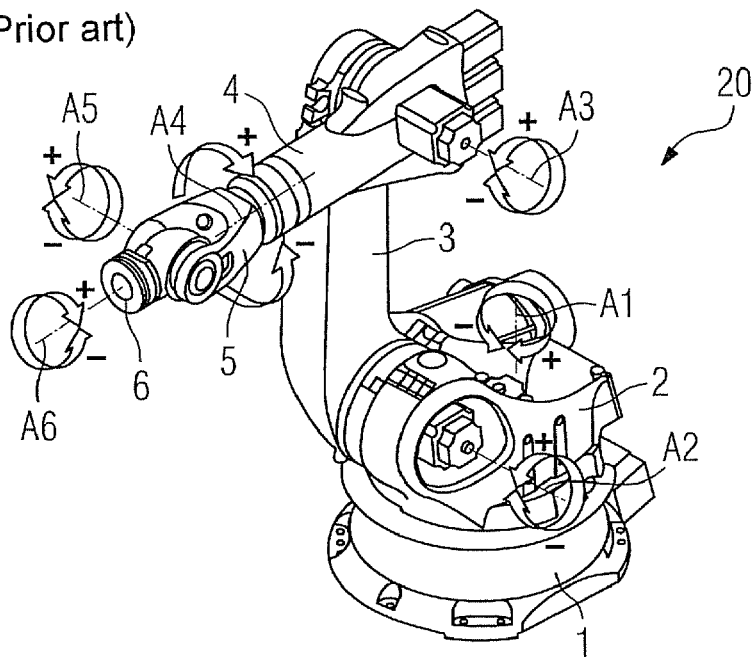
FIG. 1 shows a perspective view of an industrial robot with six axes of rotation, in accordance with the prior art.

FIG. 1 shows a familiar industrial robot 20 with six axes of rotation A1 to A6. A base frame 1, which generally has a fixed mounting on the floor, accommodates a carousel 2 which can be rotated about a first axis of rotation A1. A swivel-arm 3 is mounted on the carousel 2 so that it can swivel about a second axis of rotation A2. Affixed to the swivel-arm 3 is an arm 4, which can rotate about a third axis of rotation A3. Mounted at the end of the arm 4 is a hand 5 which can rotate about a fourth axis of rotation A4. The hand 5 has a mounting element 6 which can rotate about a sixth axis of rotation A6, which is perpendicular a fifth axis of rotation A5 about which it can swivel.

Figure 2:
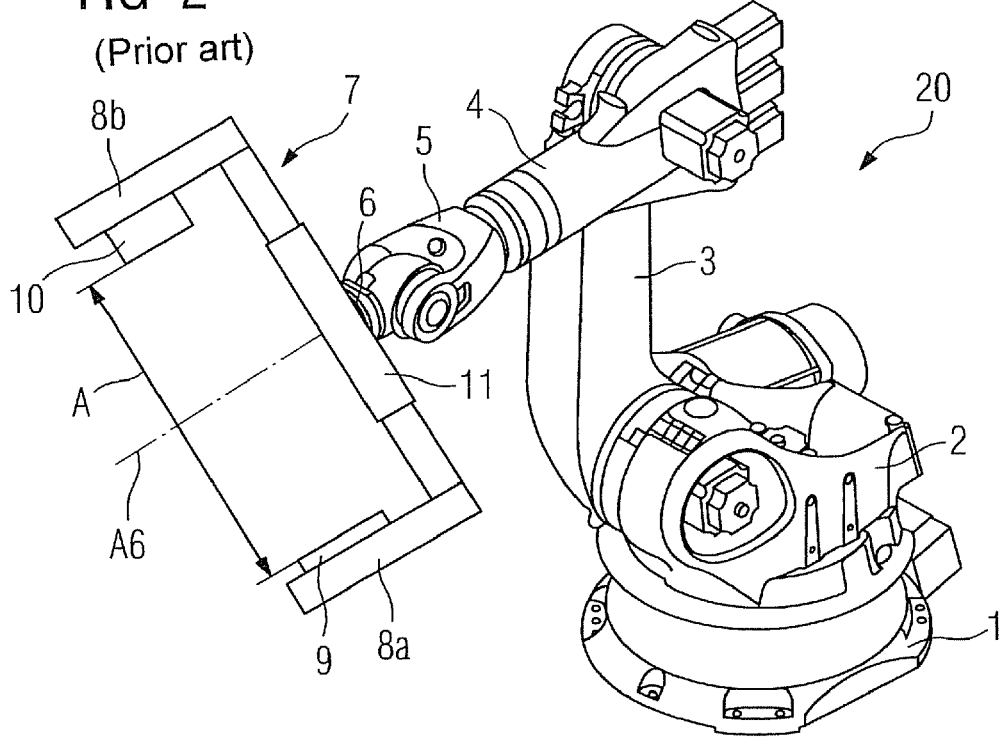
FIG. 2 shows a perspective view of an industrial robot with six axes of rotation and a bearer which carries an x-ray source and an x-ray detector in accordance with the prior art.

FIG. 2 shows a familiar industrial robot 20, on which there is a bearer in the form of a U-bracket 7 connected to the mounting element 6 of the hand 5, For this purpose a connector, which allows the bearer to be connected and disconnected and is not shown in more detail here, can be provided. The U-bracket 7 is constructed in the nature of a U-shape with two legs 8a, 8b opposite one another. Mounted on a first leg 8a can be an x-ray detector 9 and, arranged opposite this, on a second leg 8b an x-ray source 10. The first leg 8a and the second leg 8b can be mounted so as to be linearly movable in relation to a central element 11 of the U-bracket 7, so that the gap A between the x-ray detector 9 and the x-ray source 10 is adjustable.

Figure 3:
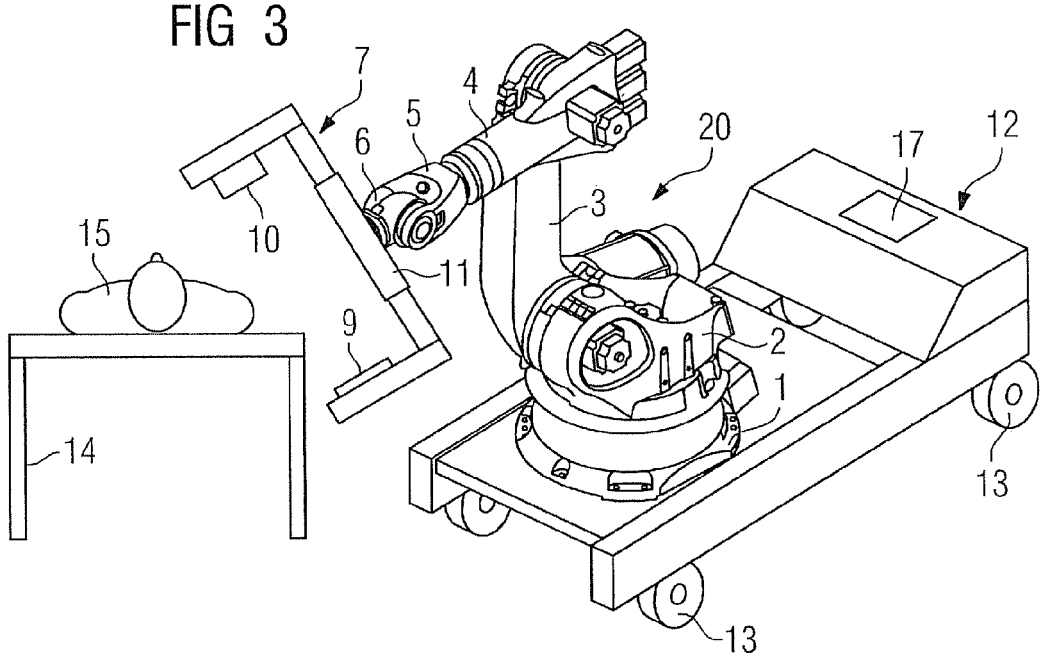
FIG. 3 shows a perspective view of an x-ray system in accordance with the invention, with an industrial robot with a U-bracket arranged on a device trolley.

As an embodiment of the invention, FIG. 3 shows an x-ray system with an industrial robot 20, arranged on a device trolley 12, which has a bearer in the form of a U-bracket with an x-ray source 10 and an x-ray detector 9. Wheels 13 enable the device trolley 12 to be driven or moved. Also arranged on the device trolley 12 are a system controller, not shown, and a display 17. An x-ray generator, an imaging system, further display units and further facility components can be arranged either externally or included on the device trolley 12. Apart from this, at least one operating unit, for example a portable remote operating unit, can be provided. In addition an integral energy supply, for example in the form of a battery or a fuel cell, can also be present.

Figure 4:
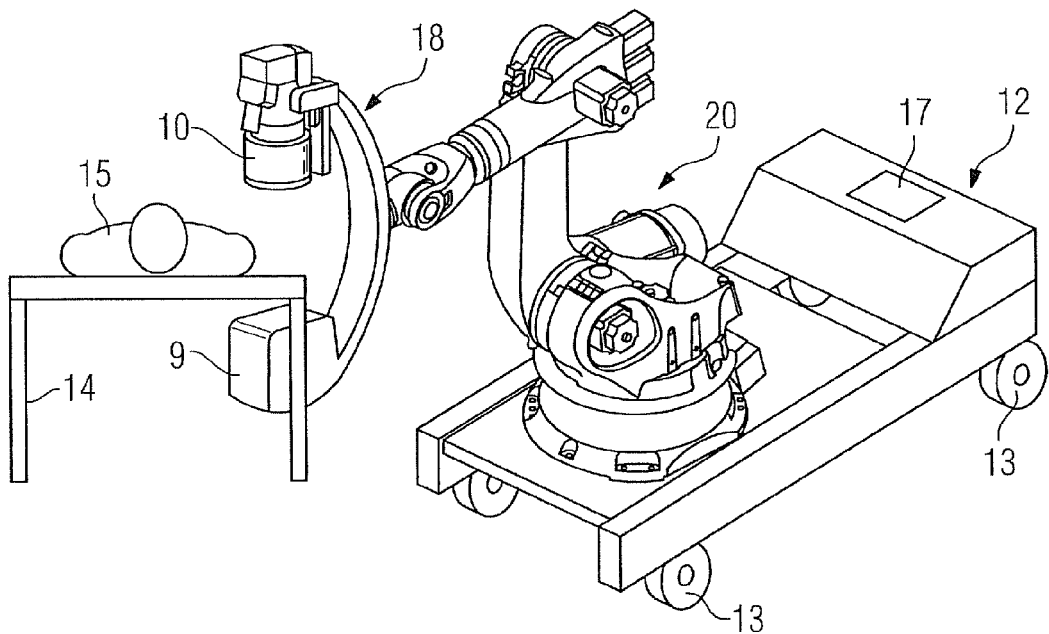
FIG. 4 shows a perspective view of an x-ray system in accordance with the invention, with an industrial robot with a C-arm arranged on a device trolley.

FIG. 4 shows another embodiment of the invention with a bearer in the form of a C-arm 18 and arranged on it an x-ray source 10 and an x-ray detector 9. With the x-ray systems shown in FIGS. 3 and 4 it is possible, even in situations where access for image recording is difficult, to achieve access possibilities, for example to a patient 15 lying on a patient table 14. Apart from this the x-ray system can, because of its mobility and drivability, be used temporarily in different rooms.

Figure 5:
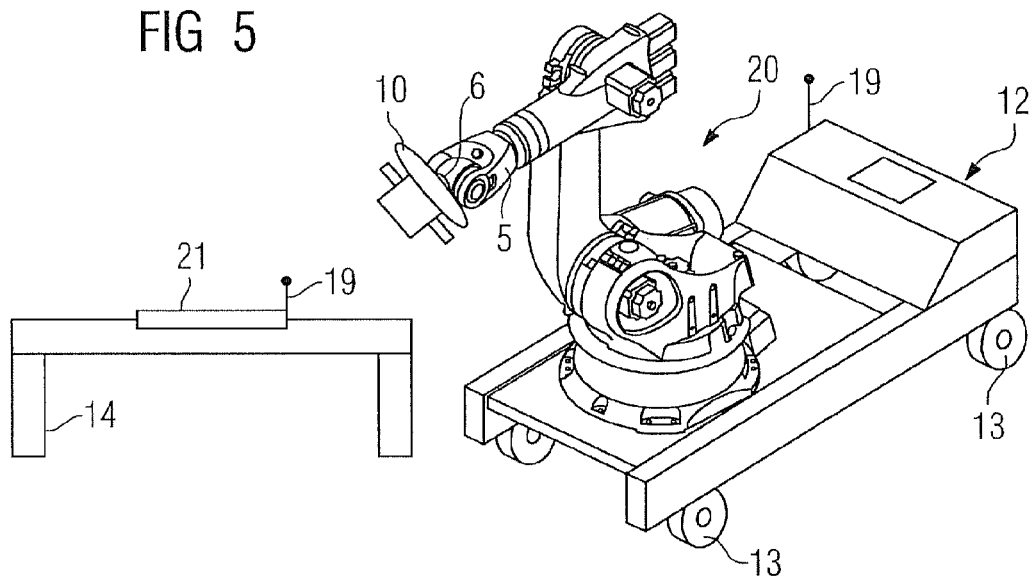
FIG. 5 shows a perspective view of an x-ray system in accordance with the invention, with a robot with an x-ray source arranged on a device trolley.
Figure 7:
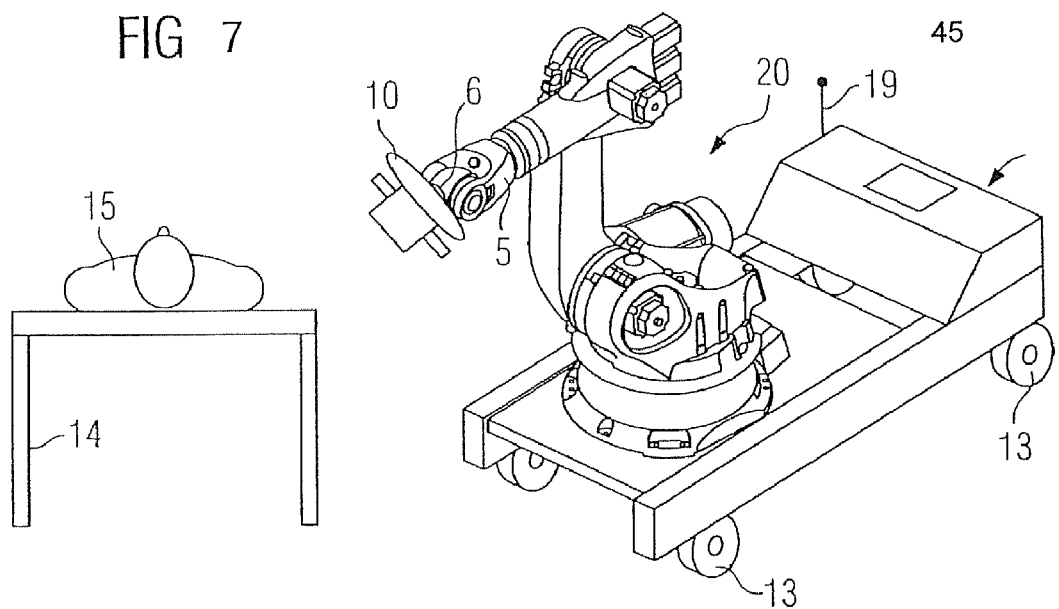
FIG. 7 shows a perspective view of an x-ray system in accord with a further embodiment of the invention.
Figure 7:
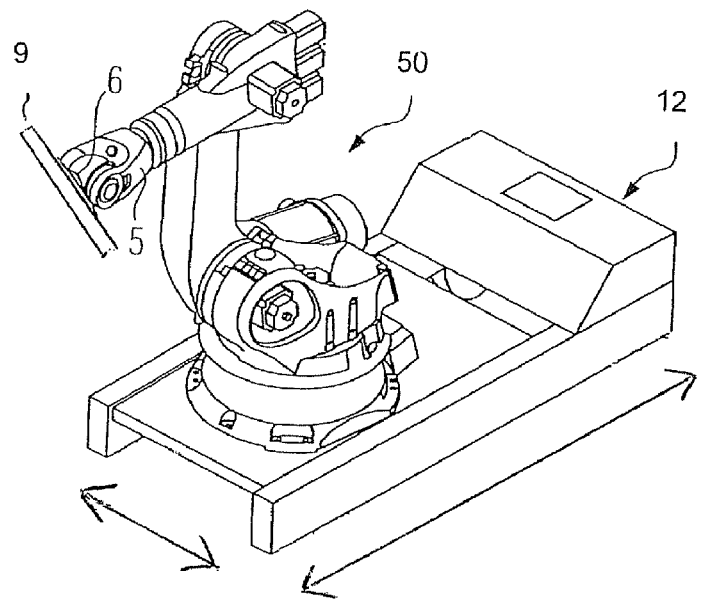

FIG. 5 shows a further x-ray system in accordance with the invention, with an industrial robot 20 arranged on a device trolley 12, where an x-ray source 10 is arranged, so that it can rotate, on the mounting element 6 of the hand 5. The x-ray source 10 is generally equipped with radiation masks and a collimator. A portable flat detector 21 is provided, separated from the device trolley or industrial robot 20, as applicable, and can be arranged as desired. The flat detector 21 and the system controller or the imaging system of the x-ray system can communicate with each other wirelessly to exchange data, for example by means of radio, a W-LAN, Bluetooth or other wireless means of communication. Optionally, a cable connection can also be provided. For a radio link, antennae 19 may for example be provided. In place of a portable flat detector 21, a second mobile industrial robot which carries the x-ray detector 9 can also be provided. See, for example, FIG. 7 which illustrates an x-ray system 45 including the combination of the afore-described robot 20 shown in FIG. 5, arranged on the device trolley 12 with the x-ray source 10, and a second independent industrial robot 50 with an x-ray detector 9. Each robot 20, 50 has at least three, and, preferably six, axes of rotation, A1-A6. See, for example, the prior art robot of FIG. 1. This arrangement makes possible independent use of the source 10 and detector 9, thus enabling an extended range of use of the system 45.

Figure 6:
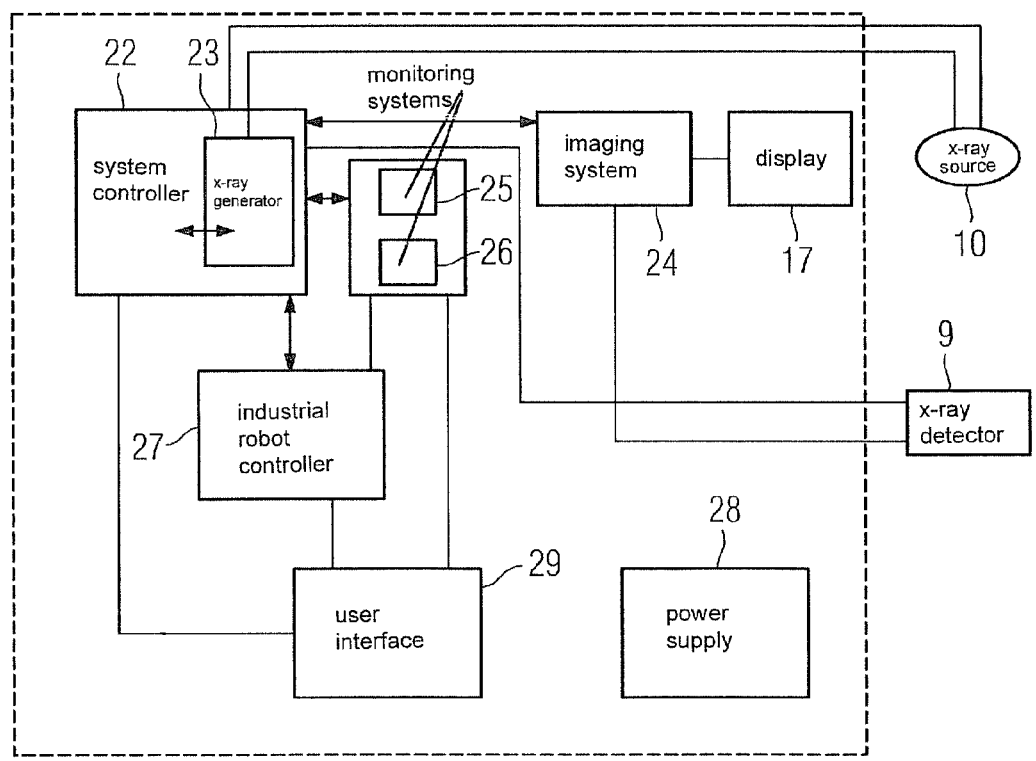
FIG. 6 shows a schematic block diagram of an x-ray system in accordance with the invention.

FIG. 6 shows a schematic block diagram of the main components of the x-ray system in accordance with the invention. A system controller 22 is linked, at least indirectly, with all the controllable components of the x-ray system. The system controller 22 communicates bidirectionally with an imaging system 24, with an industrial robot controller 27, with an x-ray generator 23 and with a collision monitoring system 25 and/or a stability monitoring system 26. By means of a user-interface 29, the user can input instructions, for example for the robot controller 27, the monitoring systems 25; 26 or the system controller, and thereby initiate various functions. Provision can also be made for actuating the device trolley using the user-interface 29.

The x-ray source 10 is supplied by the x-ray generator 23. For the purpose of transmitting image data, the x-ray detector 9 has a link to the imaging system, whereby the imaging system performs postprocessing, such as for example corrections, on the image data which is read out and then shows the x-ray images on the display 17. Apart from this, provision can be made for the x-ray system, or at least components of it, to be equipped with a cordless power supply 28. Such a cordless power supply 28 could have, for example, accumulators, batteries, or fuel cells. Provision can be made for accommodating the entire x-ray system on the device trolley 12.

The mobile industrial robot 20 or the device trolley 12, as applicable, on which the industrial robot 20 is arranged can be capable of being driven or moved either manually or by means of a motorized drive. In the case of a motorized drive, the mobile industrial robot 20 or the device trolley 12, as applicable, can have an operating unit for controlling it remotely. Instead of a device trolley, rails or tracks can also be provided, on which the mobile industrial robot 20 is driven.

In accordance with one embodiment of the invention, the industrial robot 20 or the device trolley 12 has a collision monitoring system, and at least one collision sensor for monitoring the movements of the industrial robot 20. It is especially advantageous to arrange a plurality of collision sensors, distributed over the industrial robot, for example gap sensors, which can communicate with the collision monitoring system. If one of the collision sensors reports to the collision monitoring system that a critical gap value from an external object has been passed, then the collision monitoring system sends a signal to the system controller 22 for the x-ray system. Thereupon, the system controller 22 initiates an alarm signal or stops the movement of the industrial robot 20 or steers it in another direction.

Also, in particular, for x-ray systems which have two industrial robots 20, of which one has the x-ray source 10 and the second the x-ray detector 9, the system controller 22 ensures, for example with the help of the collision sensors, that no collision occurs between the two industrial robots 20. Instructions from a user to the system controller 22 will first be checked there before actuating the relevant drive belonging to the industrial robot, by means of its drive controller, thus ensuring that there are no unwanted movements of the industrial robot 20. In addition, the drives and the industrial robots which are moved, or their joints and arm-s, as appropriate, can be equipped with sensors which supply position feedback to the drive controller and the system controller 22.

In accordance with a further embodiment of the invention, the industrial robot 20 or the device trolley 12 has a stability monitoring system and at least one stability sensor, by which the stability of the device trolley 12 can be checked. It is thus possible to prevent the industrial robot 20 from being extended to far that the device trolley becomes unstable, or collapses. The stability sensor will, for example if a first stability limit value is passed, send a message to the stability monitoring system, by which a visual or audible warning signal is initiated. If a second stability limit value is then passed, the stability monitoring system will send a signal to the x-ray system's control unit 16, which stops the movement of the industrial robot 20 or steers it in another direction.

Provision can also be made for examination rooms to have anchorage devices for the device trolley 12 or the mobile industrial robot 20, to which the device trolley 12 or the mobile industrial robot 20 can be attached temporarily for an examination; in such a situation, the stability monitoring system can be switched off.

For the purpose of operating the x-ray system, a user can select so-called examination programs or organ programs by means of the user-interface 29. These programs contain prescribed positions to which the industrial robot 20 is driven automatically, and prescribed settings with which x-ray image recordings are automatically performed. The x-ray system can have a DICOM-based interface for processing image data and items of patient information. Using the DICOM interface, image data and items of patient information can be exchanged with an external network, in particular an internal hospital network. This can be carried out either via wiring or cordlessly (radio, Bluetooth, UMTS . . . ).

Apart from a vertical buckling arm robot, a swiveling arm robot can also be provided, for example. The latter has in general four degrees of freedom, three axes of rotation and a linear axis. Equally, use could be made of a horizontal buckling arm robot.

The invention can be summarized briefly as follows: for the purpose of increasing flexibility in x-ray diagnosis, an x-ray system is provided with an x-ray source, an x-ray detector and at least one industrial robot having at least three, preferably six, axes of rotation, in which the x-ray source and/or the x-ray detector are arranged, directly or by means of a bearer, on the industrial robot, and where the industrial robot is constructed to be mobile, in particular is arranged on a device trolley.

The invention claimed is:

1. An x-ray system, comprising:
   a trolley configured with wheels for movement;
   at least a first industrial robot mounted on the trolley and having multiple rotatable arms providing the robot with at least three axes of rotation;
   an x-ray source attached to an arm of the first robot for controlled movement;
   an x-ray detector positionable with respect to the source to effect an x-ray diagnosis;
   a system controller positioned on the trolley and configured to operate at least the first robot and effect movement of the source with respect to the detector to perform the x-ray diagnosis;
   a collision monitoring system, integrally formed and operable in conjunction with the system controller, including a plurality of collision sensors configured to prevent collision between the first robot and another robot;
   position sensors mounted to the first robot to provide position information of one or more of the arms of the first robot; and
   a stability monitoring system, integrally formed and operable in conjunction with the system controller, including a stability sensor operable to prevent an arm of the first robot from being extended so far that the trolley becomes unstable or collapses, wherein a signal received from the stability sensor stops movement of the first robot,
   wherein the stability monitoring system is configured to generate a warning signal when a first stability limit is exceeded, and, whenever a second stability limit is passed, to send a signal to the system controller.

2. The x-ray system as claimed in claim 1, wherein the x-ray source and the x-ray detector are both arranged on a bearer connected to the first industrial robot.

3. The x-ray system as claimed in claim 2, wherein the industrial robot has six axes of rotation.

4. The x-ray system of claim 2, wherein the bearer is selected from the group consisting of a C-arm and a U-bracket, and wherein the x-ray source is arranged on a first end of the bearer and the x-ray detector is arranged on a second opposite end of the bearer.

5. The x-ray system as claimed in claim 1, wherein the x-ray source and the x-ray detector are both attached to the same arm of the first industrial robot via a U-shaped bearer, wherein the U-shaped bearer has a first leg and a second leg, wherein the first leg is moveable relative to the second leg.

6. The x-ray system as claimed in claim 1, wherein the trolley is driven automatically or manually.

7. The x-ray system as claimed in claim 1, wherein the industrial robot is arranged on rails or tracks.

8. The x-ray system as claimed in claim 1, further including an operating unit for controlling the system remotely.

9. The x-ray system as claimed in claim 8, wherein the trolley includes an imaging system and a display unit mounted thereon.

10. The x-ray system as claimed in claim 1, further comprising a bidirectional link to a hospital network to exchange data.

11. The x-ray system of claim 1 wherein the stability monitoring system is configured to generate an audible warning signal when the first stability limit is exceeded.

12. The x-ray system of claim 1 wherein the stability monitoring system is configured so that whenever the second stability limit is passed movement of the first industrial robot stops.

13. The x-ray system of claim 1 wherein the stability monitoring system is configured to steer the arm of the first robot in a direction different from that in which it is being extended whenever the second stability limit is passed.

14. The x-ray system of claim 1 wherein the stability monitoring system is configured to generate a visual warning signal when the first stability limit is exceeded.

15. The x-ray system of claim 1 wherein when the first stability limit is exceeded the stability sensor sends a message to the stability monitoring system, by which a visual or audible warning signal is initiated.

16. An x-ray system, comprising:
    a trolley configured with wheels for movement;

at least a first industrial robot mounted on the trolley and having multiple rotatable arms providing the robot with at least three axes of rotation;

an x-ray source attached to an arm of the first robot for controlled movement;

an x-ray detector positionable with respect to the source to effect an x-ray diagnosis;

a system controller positioned on the trolley and configured to operate at least the first robot and effect movement of the source with respect to the detector to perform the x-ray diagnosis;

position sensors mounted to the first robot to provide position information of one or more of the arms of the first robot; and a stability monitoring system, integrally formed and operable in conjunction with the system controller, including a stability sensor operable to prevent an arm of the first robot from being extended so far that the trolley becomes unstable or collapses, wherein a signal received from the stability sensor stops movement of the first robot a further industrial robot with at least three axes of rotation, wherein the x-ray source and the x-ray detector are each arranged on a different one of the industrial robots; and a collision monitoring system, integrally formed and operable in conjunction with the system controller, including a plurality of collision sensors configured to prevent collision between the first industrial robot and the further industrial robots.

\* \* \* \* \*